US00PP16163P2

(12) United States Plant Patent
Kanetsuna

(10) Patent No.: US PP16,163 P2
(45) Date of Patent: Dec. 13, 2005

(54) ***IONOCIDIUM* ORCHID PLANT NAMED 'HARURI'**

(50) Latin Name: *Ionocidium spp.*
Varietal Denomination: Haruri

(75) Inventor: Hideyuki Kanetsuna, Yamagata-gun (JP)

(73) Assignee: Sapporo Breweries Limited, Tokyo (JP)

( * ) Notice: Subject to any disclaimer, the term of this patent is extended or adjusted under 35 U.S.C. 154(b) by 17 days.

(21) Appl. No.: 10/926,571

(22) Filed: Aug. 26, 2004

(51) Int. Cl.[7] ..... A01H 5/00
(52) U.S. Cl. ..... Plt./311
(58) Field of Search ..... Plt./311

*Primary Examiner*—Anne Marie Grunberg
*Assistant Examiner*—Annette H Para
(74) *Attorney, Agent, or Firm*—Jondle & Associates P.C.

(57) ABSTRACT

A new and distinct *Ionocidium* orchid plant named 'Haruri' particularly characterized by a labellum that changes color from yellow to purple during the flowering period. Its horticultural traits further include highly irregular flowering, high productivity rate, and rapid growth in addition to economical propagation via tissue culture and vegetative division.

3 Drawing Sheets

Genus/species: *Ionocidium* spp.

BACKGROUND OF THE INVENTION

The present invention comprises a new and distinct cultivar of orchid plant, botanically known as *Ionocidium* and referred to by the cultivar name 'Haruri'. The genus *Ionocidium* is a member of the family Orchidaceae. 'Haruri' is characterized by its attractive and unique labellum which is yellow at the beginning of flowering, but in about one week becomes purple (RHS purple group, but a pinkish color). The new cultivar originated from a hybridization made in a controlled breeding program in Hiroshima, Japan in 1995. Haruri resulted from a cross between *Ionopsis utricularioides* and *Oncidium flexuosum*. Approximately 300 seedlings were produced from the hybridization in November 1996. 'Haruri' was discovered and selected as one flowering plant within the progeny of the stated cross during the flowering period from December 1997 to May 1998 in Hiroshima, Japan.

The new cultivar is a perennial and an epiphytic plant. It is used as flowering potted-plants for the home and interiorscape and to furnish cut flowers. 'Haruri' produces compound racemes with many showy flowers which open in succession beginning with the lowermost. The time of flowering is irregular with the flowering period being about 2 months. The flowers possess three sepals and 2 lateral petals. The modified abaxial petal of the flower, called the labellum, is yellow in color at the beginning of flowering, but as the days pass it undergoes a massive change and becomes purple. At the base of the labellum there is some sesamoid purple-red variegation, but this color does not change. Yellow callus is attached to the base of the labellum. The color of the lateral petals and sepals does not change. The plant grows fast and under standard growing methods, it requires 1 to 1.5 years after planting until flowering.

The new orchid cultivar 'Haruri' is different from commercially available orchids of the same type such as *Oncidium flexuosum* and *Oncidium* 'Gower Ramsey'. Comparison testing has established the following differences between the 'Haruri' and *Oncidium flexuosum:*

1. The labellum of 'Haruri' changes color from yellow to purple after flowering compared to the labellum of *Oncidium flexuosum* which remains yellow and does not change color.
2. 'Haruri' has more flowers per inflorescence than *Oncidium flexuosum.*
3. The stem of *Oncidium flexuosum* is brown, whereas that of 'Haruri' is green.
4. The upper leaf surface of 'Haruri' is deep green unlike the whitish green upper surface of *Oncidium flexuosum.*

The following differences were observed between 'Haruri' and *Oncidium* 'Gower Ramsey':

1. The labellum of *Oncidium* 'Gower Ramsey' remains yellow and does not change, whereas the labellum of 'Haruri' changes after flowering.
2. The inflorescence width of 'Haruri' is approximately half that of *Oncidium* 'Gower Ramsey'.
3. The leaf length of 'Haruri' is approximately one third that of *Oncidium* 'Gower Ramsey'.
4. The leaf of 'Haruri' is narrower and thinner than that of *Oncidium* 'Gower Ramsey'.
5. *Oncidium* 'Gower Ramsey' mainly flowers in autumn, whereas 'Haruri' flowers irregularly.

General observations: Leaves are fleshy and fast growing compared with other crosses between *Ionopsis utricularioides* and *Oncidium flexuosum*. The plant has a high productivity rate. One pseudobulb sometimes grows 5 stems. Flowering is highly irregular, and when the flowering period finishes, the plant immediately grows a new pseudobulb and flowers about half a year later.

The first successful asexual reproduction of 'Haruri' was performed by use of mericlones. This propagation took place in Hiroshima, Japan in December 1999. The characteristics as herein disclosed for 'Haruri' are firmly fixed and are retained through successive generations of asexual reproduction.

BRIEF SUMMARY OF THE INVENTION

The following traits have been repeatedly observed and determined to be basic characteristics of 'Haruri' which in combination distinguish this orchid as a new and distinct cultivar:

1. Labellum which changes color from yellow to purple after flowering.
2. Inflorescence is a compound raceme.
3. Time of flowering is highly irregular.
4. Plant has high productivity rate with as many as 5 stems growing from one pseudobulb at times.
4. Stems sometimes emerge from the top end of the pseudobulb.
5. Stems generally grow at an angle upward from the base of the pseudobulb.
6. Plant grows fast and period of cultivation can be reduced.
7. Plants may be propagated economically and uniformly using tissue culture (micropropagation) or vegetative division.

The new cultivar's flowers chang color with variations in temperature. 'Haruri' gains color at night in low temperatures. The lower the temperature, within a range of 5° C. to 15° C., the darker the purple color becomes. If the temperature is greater than 15° C., it becomes light purple. Coloring is also affected by ultraviolet (UV) radiation. In the presence of a large amount of shade, the flowers do not gain color. In a greenhouse covered with a UV reduction film, they become light purple; even in lower temperatures the reduction of UV radiation makes it difficult for the flowers to acquire color. The plant is suited for cultivation within a temperature range of 15° C. to 20° C.

BRIEF DESCRIPTION OF THE DRAWINGS

The accompanying photographs show typical plant and flower characteristics of 'Haruri' with colors being as true as is resonably possible in photographs of this character.

DETAILED BOTANICAL DESCRIPTION

Figure 1:
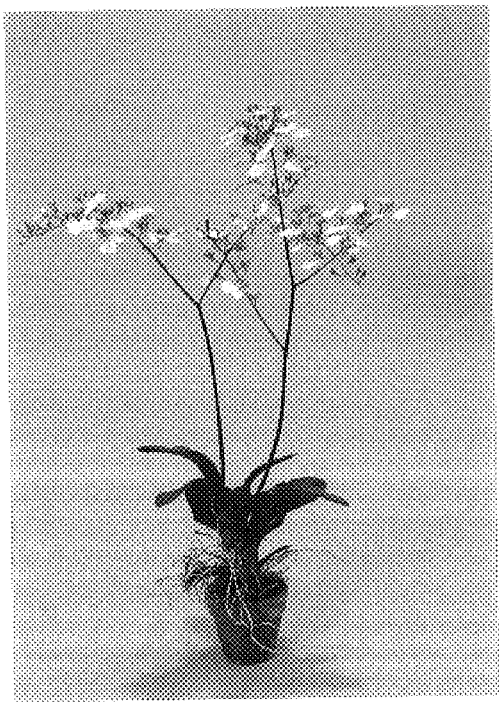
FIG. 1 shows a full size view of an entire plant of the new variety of orchid.
Figure 2:
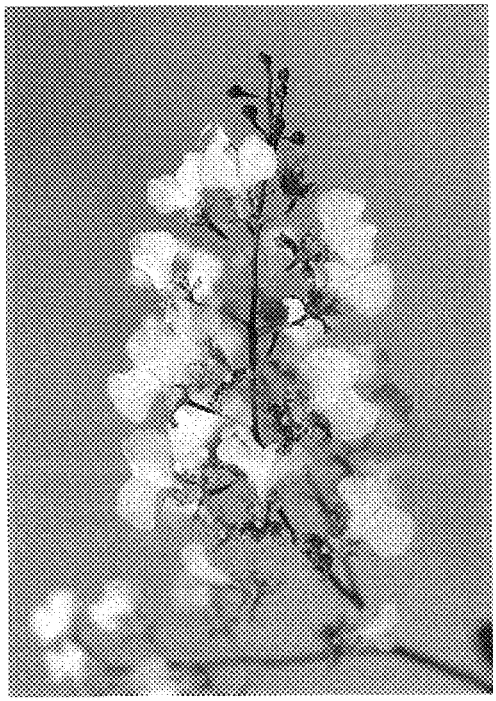
FIG. 2 shows the general appearance of typical a inflorescence.
Figure 3:
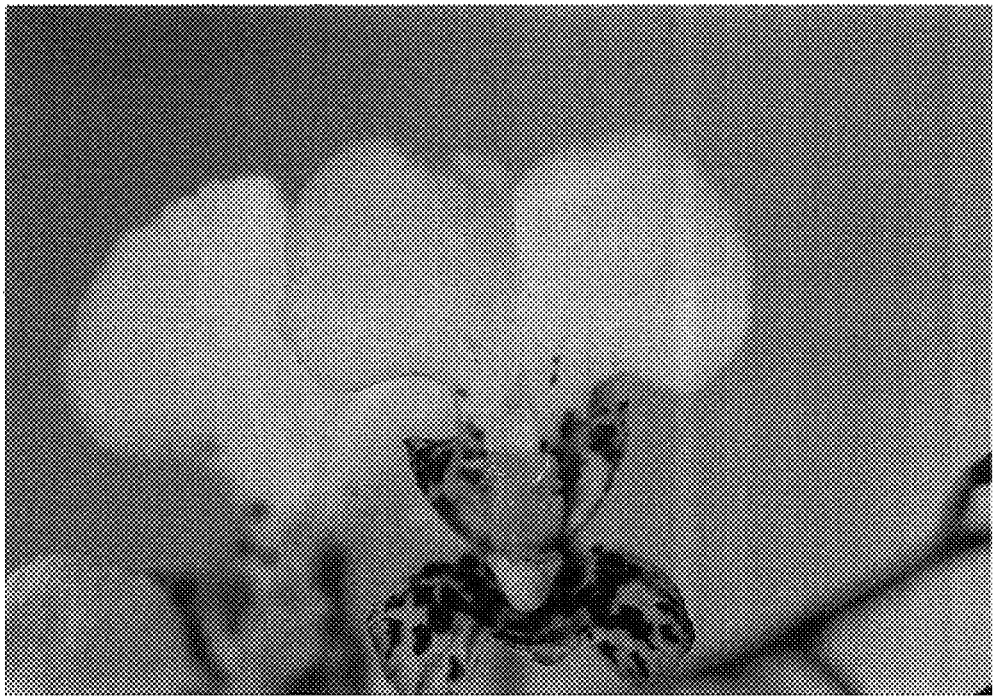
FIG. 3 shows a close-up view of the flower showing the yellow coloration which appears at the beginning of flowering.
Figure 4:
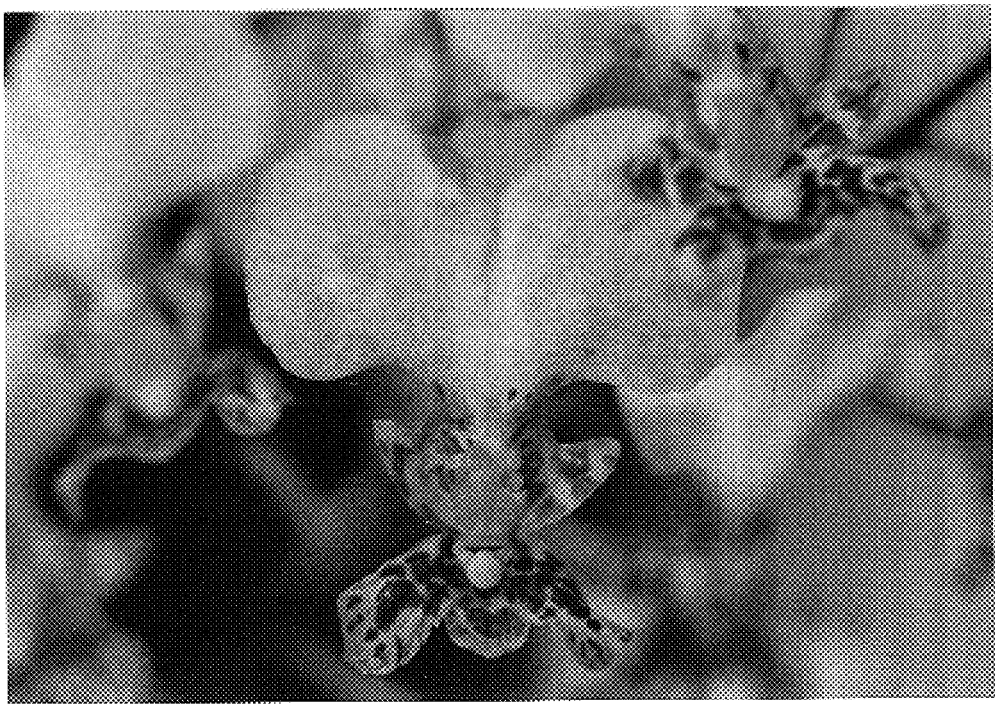
FIG. 4 shows a close-up view of the flower showing the purple coloration which appears at the later stage of flowering.
Figure 5:
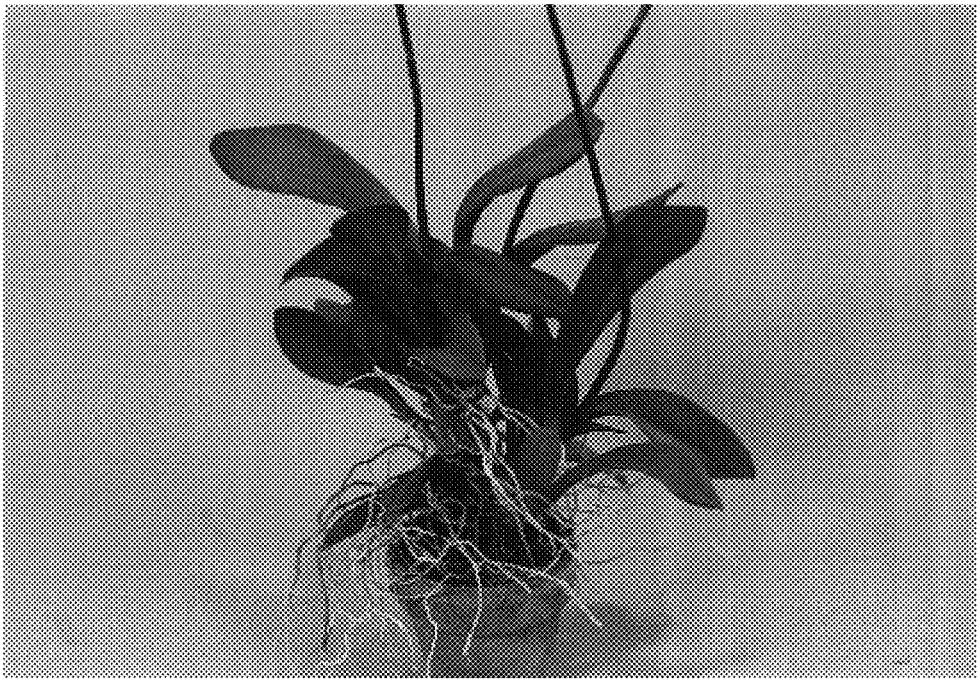
FIG. 5 shows a close-up view of the foliage and roots.
Figure 6:
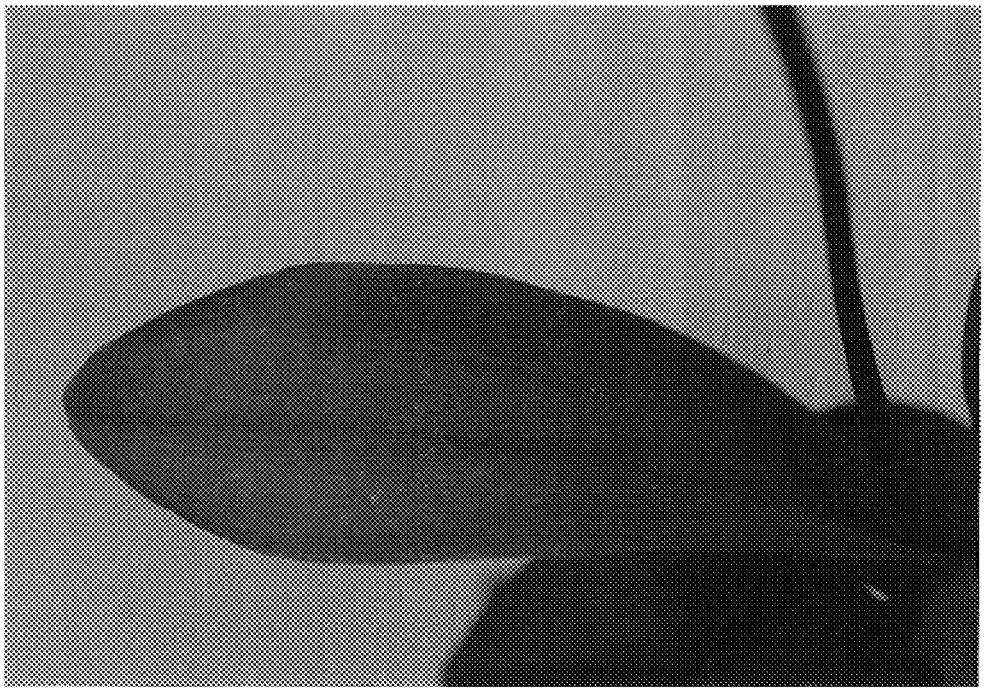
FIG. 6 shows a close-up view showing the characteristics of the leaf.

In the following description, color references are made to The Royal Horticultural Society (R.H.S.) Colour Chart. The color values were determined at about 4:00 p.m. on Jun. 14, 2004, under 10,000 lux natural light in a glasshouse at Gunma, Japan.

The following observations and measurements describe plants grown in Japan under conditions which approximate those generally used in commercial practice. The age of the observed plant, used to determine the characteristics described herein, was approximately 20 months from planting.

Classification:

*Family.*—Orchidaceae.

*Genus/species.*—*Ionocidium* hybrid cv. 'Haruri'.

Origin: Seedling from a cross between *Ionopsis utricularioides* and *Oncidium flexuosum.*

Plant:

*Propagation.*—Asexual propagation by tissue culture or division.

*Mature plant size.*—Approximately 40 to 60 cm (from the soil surface to the tip of the inflorescence) in height and width of 40 to 60 cm. Under appropriate growing conditions, plants (stocks) obtain a mature size of approximately 10 to 18 cm in height and approximately 18 to 25 cm in width. Stocks smaller than this can still be made to flower.

*Growth habit description.*—Flowers appear when the pseudobulb reaches maturity. It flowers irregularly, basically twice a year. Roots rot easily if there is constant moisture in the pot.

*Vigor.*—Strong.

Stem:

*Length.*—Approximately 30 to 50 cm long from the stem base to the tip of the inflorescence and 13 to 18 cm long from the stem base to the base of the inflorescence.

*Diameter.*—4.0 to 4.5 mm in diameter at the stem base nearest to the pseudobulb, 2.0 to 3.0 mm near the base of the inflorescence, and 1.5 mm near the tip.

*Color of stem base.*—RHS 137B (green).

*Color of stem apex.*—RHS 143B (green).

Leaves:

*Quantity.*—Usually 5 leaves are produced per pseudobulb.

*Leaf length.*—9 to 15 cm.

*Leaf width.*—2 to 4 cm.

*Leaf thickness.*—1.0 to 1.4 mm.

*Shape.*—Broad linear with an unequal obtuse apex.

*Arrangement.*—Alternate phyllotaxis.

*Color of upper leaf surface.*—RHS 137B (green). Color is the same at the base, apex and margin.

*Color of lower leaf surface.*—RHS 143A (green). Color is the same at the base, apex and margin.

*Leaf blade.*—The leaf blade is glossy and fleshy. The veins stand out from the leaf surface, forming thin lines parallel to the midribs. The leaf margin curls backward to a certain extent. Slight undulations can be seen on the leaves. Under conditions of strong light, the leaves change to a reddish brown color.

Flowers:

*Flower color.*—The labellum is RHS 2C (yellow) at the beginning of flowering, but in about one week becomes RHS 75B (purple). Sesamoid RHS 72A (red-purple) variegation appears at the base of the labellum, and does not change color. The sepals and lateral petals do not change in color.

*Number of inflorescences.*—2 to 5.

*Inflorescence description.*—Compound raceme combining 2 to 4 racemes. Approximately 15 to 30 cm long (from base to tip) and 15 to 30 cm wide (maximum width).

*Flowers per stem* (*per inflorescence*).—40 to 70.

*Petals (lateral petals).*—Petal number: 2. Petal shape: The petals are lanceolate oblong in shape with mucronate apex. Petal length: 7 to 9 mm. Petal width: 3.5 to 4.5 mm. Petal color: Upper surface: The ground color is RHS 76C (purple) with sesamoid variegation of RHS 77A (purple). Lower surface: The ground color is RHS 76B (purple) with sesamoid variegation of RHS 77A (purple).

*Sepals.*—Sepal number: 3. Sepal shape: lanceolate oblong with (Apex: Dorsal: Mucronate; Lateral: Obtuse.). Sepal length: 4 to 8 mm. Sepal width: Dorsal: 3 to 5 mm; Lateral: 2.5 to 4.0 mm. Sepal color: Upper surface: RHS 76C (purple) with sesamoid variegation of RHS 77A (purple). Lower surface: RHS 76B (purple) with sesamoid variegation of RHS 77A (purple).

*Labellum.*—The labellum extends in a heart shape with symmetrical left and right sides from the base where the callus is attached.

*Labellum width.*—18 to 22 mm in a completely extended state.

*Labellum length.*—18 to 20 mm including the base.

*Labellum color.*—Early flowering period: Upper labellum surface: RHS 2C (yellow). Sesamoid variegation RHS 72A (red-purple) appears at the base of the labellum. Lower labellum surface: RHS 4D (yellow) with fine lines of RHS 64D (red-purple variegation). Late flowering period: Upper labellum surface: RHS 75C (purple). A gradation of of RHS N78B (purple) appears spreading out from the base of the labellum. Lower labellum surface: RHS 76C (purple) with a small amount of RHS N78B (purple) gradation appearing around the base.

*Raceme dimension.*—The raceme is approximately 5 to 20 cm from base to tip, and 5 to 7 cm in diameter at the midpoint.

*Flowering time.*—First flowers can be expected approximately 12 to 18 months after planting a plant with a maximum leaf size of 5 to 7 cm in length and 2 to 3 cm in width. Flowering period is approximately 2 months.

*Lastingness of flowers.*—3 weeks on plants cultivated for 12 to 18 months; 10 to 14 days in summer and 20 to 30 days in winter.

*Fragrance.*—Absent.

*Reproductive organs.*—All reproductive organs are united into a single short structure called the column. Styles are absent. Column: Approximately 2 mm long and 2 mm wide. Color is RHS 145C (yellow-green) during the early flowering period and RHS 138C (green) in the late flowering period. Stigma: Stigmas are part of the column. Pollinia: Two, 0.4 mm in size, obovate in shape and RHS 12A (yellow) in color. Ovary: The ovary is present below the calyx and is RHS 144A (yellow-green) when not fertilized. It is 6 to 8 mm long and approximately 1.2 mm in diameter at the thickest part near the calyx. Pedicel: Approximatley 10 to 14 cm long and 0.8 mm in diameter, RHS 149D (yellow-green) in color.

Roots: Since the stock grows gradually in an upward direction, the roots appear outside of the soil. One pseudobulb initiates about 10 to 20 roots, and these divide into branches.

*Diameter.*—Approximately 1.8 mm at the base nearest to the pseudobulb and 0.5 mm at the apex.

*Root color.*—Above ground: RHS 192C (gray-green). After watering: RHS 144B (yellow-green) immediately after watering. Underground: RHS 155C (white). Roots become RHS 158B (yellow-white) immediately after watering. Root apex color: RHS 144C (yellow-green).

Growing conditions: The plant should be grown at 15 to 20° C. for 4 to 6 months after planting. Thereafter, for 6 to 12 months, the plant should be grown in a greenhouse at 10 to 15° C. to enable flowering. It takes approximately 2 weeks for plants growing in tissue culture to initiate roots.

Plant disease resistance/susceptibility: Under conditions of too much water, a variety of diseases have been observed. Soft rot symptoms due to *Pseudomonas* bacteria appear. In addition, during the flowering period, spots appear on the petals due to *Botrytis* bacteria.

I claim:

1. A new and distinct cultivar of *Ionocidium* orchid plant named 'Haruri', as illustrated and described.

* * * * *